United States Patent [19]

Stewart, II

[11] Patent Number: 5,236,707
[45] Date of Patent: Aug. 17, 1993

[54] STABILIZATION OF HUMAN INTERFERON

[75] Inventor: William E. Stewart, II, Lewisville, Tex.

[73] Assignee: Dallas Biotherapeutics, Inc., Dallas, Tex.

[21] Appl. No.: 790,670

[22] Filed: Nov. 8, 1991

[51] Int. Cl.$^5$ .............................................. A61K 45/02
[52] U.S. Cl. ................... 424/85.7; 424/85.4; 530/351
[58] Field of Search ............... 530/351; 424/85.4, 85.7

[56] References Cited

U.S. PATENT DOCUMENTS

| | | | |
|---|---|---|---|
| 3,981,991 | 9/1976 | Stewart | 424/85.4 |
| 4,675,184 | 6/1987 | Hasegawa et al. | 424/85.4 |
| 4,680,175 | 7/1987 | Estis et al. | 424/85.4 |
| 4,957,734 | 9/1990 | Miller | 424/85.4 |
| 5,165,921 | 11/1992 | Ganesh et al. | 424/85.7 |

FOREIGN PATENT DOCUMENTS 0077063  4/1983  European Pat. Off. .

OTHER PUBLICATIONS

Stewart et al., Proc. Natl. Acad. Sci. 74:4200 (1977).
Stewart II, W. E., pp. 17–18 *The Interferon System*, Springer-Verlag (2nd Ed. 1981).
Adolf et al., J. Interferon Res. 10 (Supp. 1):S57 (1990).
Stewart and Stewart, Virology 97:473 (1979).

*Primary Examiner*—Jeffrey E. Russel
*Assistant Examiner*—Lynn Touzeau
*Attorney, Agent, or Firm*—Baker & Botts

[57] ABSTRACT

Described herein are compositions for stabilizing human interferon, including pharmaceutical preparations useful in topical applications. Amine stabilizing agents such as primary aliphatic amines and anionic stabilizing agents such as lithium organo sulfates protect human interferons from degradation and provide enhanced storage stability. These stabilizing agents containing interferon can be added to appropriate pharmaceutical carriers for topical applications. The topical products also exhibit enhanced storage stability.

34 Claims, No Drawings

STABILIZATION OF HUMAN INTERFERON

TECHNICAL FIELD OF THE INVENTION

This invention relates to the stabilization of human interferon, and more particularly, to alpha interferon and omega interferon or mixtures thereof.

BACKGROUND OF THE INVENTION

Interferons are proteins having a variety of biological actions including antiviral, immunomodulating and antiproliferative effects. Cellular production of interferons may be stimulated by numerous agents, including viruses. Interferons protect animal tissues and cells against viral attack and are an important host defense mechanism. Interferon may be produced endogenously by numerous cell types such as leukocytes, fibroblasts and lymphocytes, and may also be produced in cell culture or recombinantly. In most cases, interferons provide better protection to tissues and cells of the kind from which they have been produced than to other types of tissues and cells, indicating that human-derived interferon should be more efficacious in treating human diseases than interferons from other species. There are several distinct types of interferons, generally classified as alpha, beta, gamma and omega interferons, and a large number of variants thereof.

The alpha and omega interferons are derived primarily from leukocytes. Cell-derived interferon such as leukocyte interferon is difficult to purify to homogeneity and, as a consequence, is most often used as a crude or partially purified preparation. Leukocyte interferon preparations contain two molecular populations (alpha and omega interferons) that are distinguishable physically, chemically and biologically. Alpha interferon comprises approximately 80% of leukocyte interferon activity, and omega interferon comprises about 20% of leukocyte interferon activity. The leukocyte interferon forms can be separated by sodium dodecyl sulfate-polyacrylamide gel electrophoresis (SDS-PAGE) into slow- and fast-migrating components as described by Stewart II, W. E. and Desmyter, *J. Virology* 67:68–73 (1975). The larger leukocyte interferon forms have apparent molecular weights of about 21,000–25,000 Daltons, while the smaller leukocyte interferon forms have apparent molecular weights of about 15,000–18,000 Daltons. The larger (omega) interferon are glycosylated, whereas the smaller (alpha) interferon are not. General discussions of these and other interferons can be found in various texts and monographs including: *The Interferon System* by W. E. Stewart, II, Springer-Verlag, New York (1979); and *Interferon Therapy*, World Health Organization Technical Reports Series 676, World Health Organization, Geneva (1982).

The method of administering interferon is an important factor in the clinical application of this important therapeutic agent. Systemic administration of interferon by either intravenous, intramuscular or subcutaneous injection has been most frequently used with some success in treating disorders such as hairy cell leukemia and Acquired Immune Deficiency Syndrome (AIDS)—related Kaposi's sarcoma. Among the problems inherent in intravenous, intramuscular or subcutaneous administration is that interferon can come into contact with uninfected or nonmalignant cells, and may thereby cause unwanted side effects such as fever, malaise and myalgia.

In some cases it would be preferable to administer interferon directly to the affected tissues or organs. This may be accomplished by direct injection of interferon into the diseased site such as done in selected cases of condylomata acuminata (genital warts), involving the external surfaces of genital or perianal areas. Interferon can also be administered by local topical application directly to the diseased site, such as a viral-induced skin lesion. Topical interferon may be useful for treatment of conditions such as condylomata acuminata, cervical dysplasia, rectal cancer, basal cell carcinoma, penile cancer or any other disorder responsive to interferon, particularly those linked to papilloma virus infection. Topical application in these cases could reduce the unwanted side effects associated with intramuscular, intravenous or subcutaneous administration. Also, the patient could self-administer topical interferon without the direct assistance of a qualified health-care worker. A topical interferon product could also promote patient compliance by providing a more pleasant therapeutic experience for the patient than interferon treatment via injection.

The lack of interferon stability in solutions and other products has heretofore limited its utility. Interferon products having enhanced storage stability should facilitate more wide-spread use of this important therapeutic agent. Several factors are important in designing a useful topical interferon preparation. First, conventional topical interferon preparations are generally considered unstable, and therefore are considered to have a limited shelf-life. A topical interferon preparation should be stabilized to prevent degradation over time and upon shipping and handling. Second, because interferon generally has a higher molecular weight than the molecular weights of the therapeutic agents usually administered in topical preparations, interferon should be incorporated into a substance which sufficiently holds the high molecular weight interferon in suspension during packaging, shipping and application, and yet also be able to release the substance from the preparation in a reasonable length of time once it has been applied to the diseased site. Third, the preparation must not adversely affect the antiviral activity of interferon.

The present invention describes new, improved stabilizers and methods for stabilizing interferon, meeting the requirements for topical interferon products defined above and for stabilized interferon solutions.

Other interferon-stabilizing agents have been described and used to stabilize interferon.

Estis et al. in U.S. Pat. No. 4,680,175 describe the use of protease inhibitors such as alpha-1-antitrypsin inhibitor, alpha-2 macroglobulin, soybean inhibitor, N-alpha-tosyl-L-lysine chloromethyl ketone, phenylmethylsulfonyl fluoride, and N-alphatosylphenylalanine chloromethyl ketone to stabilize topical interferon preparations. Miller, in U.S. Pat. No. 4,957,734, discloses the use of anionic, cationic and nonionic surface active agents but claims no stabilization of interferon. Miller discloses that quarternary ammonium detergents such as cetyl pyridinium chloride and benzalkonium chloride are preferable cationic agents. Hasegawa et al. in U.S. Pat. No. 4,675,184 teach that anionic surface active agents such as sodium alkyl sulfates stabilize betainterferon (fibroblast-derived) but only in conjunction with a polyhydric sugar alcohol and an organic buffer as stabilizers.

Stewart et al. in U.S. Pat. No. 3,981,991 teach that interferon can be stabilized by treating the antiviral agent with a combination of: 1) guanidine-hydrochloride or urea; 2) mercaptoethanol or ethanethiol; and 3) an agent selected from the group consisting of sodium dodecylsulfate, sodium decylsulfate, sodium dodecylsulfonate, dodecylamine and decylamine. Stewart et al. caution that interferon cannot be stabilized with only one or two of the aforesaid three agents.

None of these patents teach that human alpha and omega interferons or mixtures thereof can be stabilized with only the stabilizing agents described herein.

SUMMARY OF THE INVENTION

This invention relates to preparations for stabilizing human interferon. The present invention shows that human alpha and omega interferon, or mixtures thereof, can be stabilized when placed in solutions containing amines, and more particularly, primary aliphatic amines having from between 8 to 14 carbon atoms. Lithium salts of anionic stabilizing agents such as lithium organo sulfates also stabilize interferon. Stabilized interferon may be placed in a pharmaceutically acceptable carrier for topical administration. Further stability is achieved by adding additional amine-stabilizing agents to the stabilized interferon product.

These and other advantages of the present invention will become apparent from the following detailed description.

DETAILED DESCRIPTION OF THE INVENTION

The present invention relates to stabilizing interferon to enhance its storage stability. This invention is applicable to all types of interferon including natural interferon, interferon produced by recombinant DNA technology, and interferon produced by chemical synthesis or modification. Also, the invention can be used with crude, semi-purified and purified interferon from leukocytes, fibroblasts, lymphocytes or any other interferon-containing or producing tissues from humans or any other appropriate species.

A method for producing interferon from leukocytes (comprising alpha interferon and omega interferon) is described by Cantell, et al. in: *Methods in Enzymology*, 78: 29–38 (1981). In general, the interferon produced by this method and other methods is supplied as a liquid. Alpha isolates and omega isolates of interferon are prepared by subjecting leukocyte interferon to non-reducing sodium dodecyl sulfate-polyacrylamide gel electrophoresis (SDS-PAGE) as described in Stewart, W. E. II, et al., *Proc. Natl. Acad. Sci.* 74:4200–4204 (1977). Briefly, leukocyte interferon samples in 0.01M sodium phosphate buffer were constituted to contain 5M urea and 1% sodium dodecyl sulfate. Bromphenol blue in sucrose was added to make the samples 6% sucrose, and the samples were heated to 100° C. for one minute. Aliquots of 0.1 ml of sample were electrophoresed on parallel SDS-PAGE gels. When the dye front had migrated about 18 centimeters into gels, gels were sliced into 2.2 millimeter segments, and two adjacent slices were pooled into each fraction containing the alpha isolates and omega isolates, and were eluted overnight at 4° C. into 1 ml of Eagle's minimal essential medium containing 10% fetal calf serum.

Those skilled in the art will recognize that the amount of interferon which is administered in any particular case, as well as the frequency at which the interferon is administered, will depend upon such factors as the type of interferon used, the disease being treated, the patient's response to interferon treatment, and whether the preparation used is a semi-solid or a liquid. The National Institutes of Health (United States Department of Health and Human Services, Bethesda, Md.) have established unit strengths for interferon activity. In terms of these unit strengths, dosage levels for topical pharmaceutical preparations using crude or partially purified natural interferons can range from about 10,000 IU/gram of topical preparation to 1,000,000 IU/gram of topical preparation.

The term "stabilized interferon composition" is employed herein to describe an agent having an interferon and an amine stabilizing agent present in an effective amount to stabilize interferon. The interferon can be human interferon or interferon from any other appropriate species. Preferably the interferon is human leukocyte-derived interferon comprising alpha interferon, omega interferon or mixtures thereof. The interferon can also be recombinant interferon or interferon produced or modified chemically. The present invention reveals enhanced storage stability and antiviral activity of stabilizing agents for interferon.

The term "amine stabilizing agent" is employed herein to include primary, secondary, or tertiary amines. Preferably, the amine stabilizing agent is a primary amine having the general formula $RNH_2$ where "R" is an aliphatic group. Preferably, amine stabilizing agents have aliphatic groups of from about 8 to about 14 carbon atoms, although aliphatic groups having less than 8 or more than 14 carbon atoms are encompassed within the scope of this invention. More preferably, aliphatic primary amines having from between about 8 to about 14 carbon atoms may be used as amine stabilizing agents. Most preferably, the amine stabilizing agent is a primary aliphatic amine having an aliphatic group consisting of 12 carbon atoms. The aliphatic groups may be linear or branched, but are preferably linear. Representative examples of amines useful as amine stabilizing agents include octyl amine, decyl amine, dodecyl amine, and tetradecyl amine. Amine stabilizing agents having more than 14 carbon atoms are generally insoluble. Amine stabilizing agents having less than 8 carbon atoms are generally inefficient stabilizers. Most preferable of the amine stabilizing agents is dodecyl amine. The effective amount of amine stabilizing agents to stabilize interferon ranges from about 0.1% to about 10.0% by weight, although lower or higher concentrations of amine stabilizing agents may be used, as would be ascertainable by a person having ordinary skill in the art.

The term "lithium stabilized interferon composition" is employed herein to describe an agent having an interferon and a lithium anionic stabilizing agent present in an effective amount to stabilize interferon. The interferon can be human interferon or interferon from any other appropriate species. Preferably the interferon is human leukocyte-derived interferon containing alpha interferon or omega interferon or mixtures thereof. The interferon can also be recombinant interferon or interferon produced or modified chemically.

The term "lithium anionic stabilizing agent" is employed herein to include the lithium salts of compounds having a net negative charge. Lithium anionic stabilizing agents useful in this invention are lithium organo sulfates, and may be represented by the general formula:

$$Li_nRX$$

where "R" is an aliphatic group, "X" is an anion and "n" is chosen to electrochemically balance the anion. "X" is preferably sulfate. Lithium anionic stabilizing agents containing aliphatic groups having from about 8 to about 22 carbon atoms may be used, although aliphatic groups of more than 22 carbons or less than 8 carbons are encompassed within the scope of the present invention. Preferably, lithium anionic stabilizing agents contain 8 to 14 carbon atoms, and most preferably 12 carbon atoms. Representative examples of lithium anionic stabilizing agents include lithium octyl sulfate, lithium decyl sulfate, lithium dodecyl sulfate and lithium tetradecyl sulfate. The concentrations of lithium anionic stabilizing agents may range from about 0.1% to about 10.0% by weight, although lower or higher concentrations may be used as would be ascertainable by a person having ordinary skill in the art. The patent of Hasegawa et al., described above, does not disclose the use of lithium organo sulfate interferon stabilizers. As will be noted below, lithium-containing stabilizing agents have a clinical utility not possessed by sodium-containing stabilizing agents.

Interferon compositions containing from about $1 \times 10^4$ to $1 \times 10^6$ IU/ml are most preferably used in the present invention, although interferon compositions having lower or higher activity may also be used as would be readily ascertainable by a person having ordinary skill in the art.

The precise mechanism of action of the amine stabilizing agents and lithium anionic stabilizing agents in stabilizing interferon is not known, but is thought to be related to "defensive reversible denaturation" as described by W. E. Stewart II, et al. *Nature*, Vol. 249, pp. 460–61 (1974) and W. E. Stewart II, et al., *Preparative Biochemistry* Vol. 4, pp. 383–93 (1974) which are each herein specifically incorporated by reference.

The clinical utility of sodium-containing interferon stabilizing agents such as sodium organo sulfates is limited by the side effects associated with topical administration of sodium-salt-containing products. A not uncommon unwanted side effect associated with use of sodium-salt-containing products is chronic irritant dermatitis. Tupker, R. A. et al., *Acta Derm. Venereol.* 70:1–5 (1990). Unlike sodium-salt-containing topical products, lithium-salt preparations are not associated with such unwanted side effects. A lithium-salt-containing interferon product would therefore represent an advance over sodium-salt-containing topical interferon preparations.

The term "interferon antiviral preparation" as used herein describes a product having a stabilized interferon composition and a pharmaceutically acceptable carrier, said pharmaceutically acceptable carrier itself containing substantially little or no amine stabilizing agent in the absence of the stabilized interferon composition. Effective amounts of amine stabilizing agent for stabilizing interferon in an interferon antiviral preparation are achieved when the weight of amine stabilizing agent exceeds the weight of total protein. Total protein may be determined by conventional techniques generally known to those skilled in the art. For example, total protein may be determined by the Lowry method or modifications thereof. Effective amounts of amine stabilizing agent (gram amine stabilizing agent per gram total protein) range from about 1.0 to about 10.0, and are most preferably about 1.44.

The term "lithium stabilized interferon antiviral preparation" as used herein describes a product having a lithium stabilized interferon composition and a pharmaceutically acceptable carrier, said pharmaceutically acceptable carrier itself containing substantially little or no lithium anionic stabilizing agent in the absence of the lithium stabilized interferon composition. Effective amounts of lithium stabilizing agent for stabilizing interferon in a lithium stabilized interferon antiviral preparation are achieved when the weight of lithium stabilizing agent exceeds the weight of total protein. Total protein may be determined by conventional techniques generally known to those skilled in the art. For example, total protein may be determined by the Lowry method or modifications thereof. Effective amounts of lithium stabilizing agent (gram lithium stabilizing agent per gram total protein) range from about 1.0 to about 10.0, and are most preferably about 1.44.

Pharmaceutically acceptable carriers should be inert. The carrier should not react with or otherwise reduce the effectiveness of the active ingredients, and more particularly, should not significantly diminish the effectiveness or stability of the interferon. Pharmaceutically acceptable carriers include water, ethanol, polyethylene glycol, mineral oil, petrolatum, propylene glycol, lanolin, and similar agents. Appropriate preparations for topical applications are preferably constituted in lotion, cream, oil or emulsion formulations.

The term "interferon ointment" as used herein describes an interferon antiviral preparation containing an amine stabilizing agent which has been added in an effective amount to the pharmaceutically acceptable carrier to stabilize interferon. The concentration of amine stabilizing agent added to the pharmaceutically acceptable carrier may range from about 0.1% to about 10.0% by weight, although lower or higher concentrations may be used depending on application.

The term "lithium interferon ointment" as used herein describes a lithium interferon antiviral preparation containing a lithium anionic stabilizing agent which has been added in an effective amount to the pharmaceutically acceptable carrier to stabilize interferon. The concentration of lithium anionic stabilizing agent added to the pharmaceutically acceptable carrier may range from about 0.1% to about 10.0% by weight, although lower or higher concentrations may be used as would be ascertainable by a person having ordinary skill in the art.

The term "mixed interferon ointment" as used herein describes an interferon antiviral preparation containing a lithium anionic stabilizing agent which has been added in an effective amount to the pharmaceutically acceptable carrier to stabilize interferon, or a lithium interferon antiviral preparation containing an amine stabilizing agent which has been added in an effective amount to the pharmaceutically acceptable carrier to stabilize interferon, or mixtures thereof. The concentration of lithium anionic stabilizing agent or amine stabilizing agent added to the pharmaceutically acceptable carrier may range from about 0.1% to about 10.0% by weight, although lower or higher concentrations may be used as would be ascertainable by a person having ordinary skill in the art.

The antiviral activity of interferon may be determined by a number of methods such as those described more fully in: W. E. Stewart II, *The Interferon System*, Springer-Verlag (2d Ed. 1981). The Cytopathic Effect Inhibition Assay (CPE) is particularly useful for determining interferon antiviral activity. The method is described more fully in Id. at pp. 17–18 and is incorporated herein by reference. As used herein, the CPE method entails introducing 50 microliters of growth medium (Eagle's minimal essential medium supplemented with 5% to 10% fetal calf serum) per well into microtiter plates. Twenty-five microliters of interferon is introduced into the first well of the microtiter row and the solution mixed with a fresh micro pipette tip. A 25 microliter aliquot is transferred to the next well and mixed with a fresh micro pipette tip. Virus controls, cell controls and standards are treated similarly. The samples are exposed to sterilizing ultraviolet radiation (approximately 6 minutes at 15 centimeters with a General Electric germicidal lamp). Freshly trypsinized cell suspensions of human foreskin fibroblast cells are introduced into each well (0.01 milliliters containing about $2 \times 10^4$ cells) and the microtiter trays are incubated over night at 37° C. A suspension of vesicular stomatitis virus (American Type Culture Collection, Camden, N.J., U.S.A.) containing about $1 \times 10^4$ plaque-forming units in 50 microliters of serum-free Eagle's minimal essential medium is introduced into each well, except cell controls, and the trays are incubated for approximately 24 hours at 37° C., at which time virus controls show 100% CPE. End-points are read microscopically as 50% protection. Residual activity thus measured is compared to the International Reference standard 6, 69/19 for human interferon (leukocyte-derived, Medical Research Council, National Institute for Biological Standards and Control, London, U.K.) tested simultaneously.

Because of the recognized inaccuracies of this biological assay (differences of less than 0.3 $\log_{10}$ cannot be objectively distinguished), all results are presented as approximate percentages of starting interferon activities. Thus, a reading of 100% activity indicates no detectible or significant loss of interferon activity. A reading of between 70 and 80% activity indicates a slight loss of interferon activity; a reading of between 30 to 60% activity indicates a significant detectible loss; a reading of between 1 to 20% activity indicates approximately a 1 to 2 $\log_{10}$ decrease in interferon activity; and a reading of 0% activity indicates no detectible activity remaining.

The following examples serve to illustrate embodiments of this invention without limiting the same, but should not be considered as a limitation on the scope of the invention.

EXAMPLE 1

Storage stability of interferon in stabilized interferon compositions and lithium stabilized interferon compositions was assessed. Human leukocyte interferon containing approximately 80% alpha interferon and approximately 20% omega interferon, prepared as described by Cantell, supra, was dialyzed in physiological saline. Stabilized interferon compositions were prepared by mixing aliquants of 0.1 ml human leukocyte interferon (at $1 \times 10^4$, $1 \times 10^5$ or $1 \times 10^6$ IU/ML) with 0.9 ml physiological saline (pH 7.2) containing amine stabilizing agents at the concentrations indicated in Table 1. Lithium stabilized interferon compositions were prepared by mixing aliquants of 0.1 ml human leukocyte interferon (at $1 \times 10^4$, $1 \times 10^5$ or $1 \times 10^6$ IU/ml) with 0.9 ml physiological saline (pH 7.2) containing the lithium anionic stabilizing agents at the concentrations indicated in Table 1.

The stabilized interferon compositions and lithium stabilized interferon compositions were incubated at room temperature (20° to 24° C.) for 1 hour, 24 hours, or 1 month, and then tested for residual antiviral activity using vesicular stomatitis virus and human skin fibroblast cell lines, according to the CPE inhibition method described above. Results, expressed as % of initial antiviral activity, are shown in Table 1.

TABLE 1

| Stabilization of human interferon (20–24° C.) | | | | |
|---|---|---|---|---|
| | Concentr. stabilizer | % Initial Activity storage time | | |
| Stabilizer | (wt. %) | 1 hr | 24 hr | 1 mo. |
| Lithium octyl sulfate | 0.1 | 90 | 10 | 0 |
| | 1.0 | 100 | 70 | 10 |
| | 10.0 | 100 | 100 | 60 |
| Lithium decyl sulfate | 0.1 | 100 | 30 | 10 |
| | 1.0 | 100 | 80 | 40 |
| | 10.0 | 100 | 100 | 80 |
| Lithium dodecyl sulfate | 0.1 | 100 | 100 | 100 |
| | 1.0 | 100 | 100 | 100 |
| | 10.0 | 100 | 100 | 100 |
| Lithium tetradecyl sulfate | 0.1 | 100 | 100 | 100 |
| | 1.0 | 100 | 100 | 100 |
| Octyl amine | 0.1 | 70 | 20 | 0 |
| | 1.0 | 80 | 50 | 10 |
| | 10.0 | 100 | 70 | 10 |
| Decyl amine | 0.1 | 80 | 30 | 10 |
| | 1.0 | 80 | 50 | 10 |
| | 10.0 | 100 | 70 | 30 |
| Dodecyl amine | 0.1 | 100 | 100 | 100 |
| | 1.0 | 100 | 100 | 100 |
| | 10.0 | 100 | 100 | 100 |
| Tetradecyl amine | 0.1 | 100 | 100 | 100 |
| | 1.0 | 100 | 100 | 100 |
| Control | — | 100 | 30 | 0 |

As shown, the lithium organo sulfates are effective in stabilizing the aqueous human interferons. Most effective was lithium dodecyl sulfate and lithium tetradecyl sulfate, at concentrations ranging from 0.1 to 10% by weight. The amine stabilizing agents likewise stabilized human interferon. Most effective was dodecyl amine at concentrations of 0.1% to 10% by weight, and tetradecyl amine in concentrations of 0.1% to 1.0% by weight.

EXAMPLE 2

The stabilized interferon compositions (containing dodecyl amine at 0.1% and 1.0% by weight), prepared as described in Example 1, were stored at 37° C. for 1 hour, 24 hours, or 1 month, and tested for residual antiviral activity using the CPE inhibition assay. Unstabilized interferon in saline served as a control. Results, expressed as % of initial antiviral activity, are shown in Table 2.

TABLE 2

| Stability of Stabilized Interferon Compositions (37° C.) | | | | |
|---|---|---|---|---|
| | Stabilizer Concentr. | % Initial Activity storage time | | |
| Stabilizer | (% by wt.) | 1 hr | 24 hr | 1 month |
| Dodecyl amine | 0.1 | 100 | 100 | 100 |
| | 1.0 | 100 | 100 | 100 |
| Control | — | 100 | 30 | 0 |

As shown, dodecyl amine at concentrations of 0.1% and 1.0% by weight stabilized the interferon stored at 37° C.

EXAMPLE 2

The stabilized interferon compositions prepared as described in Example 1 were stored at 56° C. for 1 hour or 24 hours, and tested for residual antiviral activity as shown in Table 3. Unstabilized interferon in saline served as a control. Results are expressed as % of initial antiviral activity.

TABLE 3

Stability of Stabilized Interferon Compositions (56° C.)

| Stabilizer | Stabilizer Concentr. (% by wt.) | % Initial Activity storage time | |
|---|---|---|---|
| | | 1 hr | 24 hr |
| Dodecyl amine | 0.1 | 100 | 100 |
| | 1.0 | 100 | 100 |
| Control | — | 3 | 0 |

As shown, dodecyl amine at concentrations of 0.1% to 1.0% by weight stabilized human interferon stored for up to 24 hours.

EXAMPLE 4

Storage stability of interferon antiviral preparation was assessed. Stabilized interferon composition, prepared as in Example 2, and a control interferon in saline were each dialyzed against 0.03M ammonium bicarbonate buffer (pH 7.6) and lyophilized. The stabilized interferon composition and control interferon in powder form were each added to a pharmaceutical carrier comprising (weight %) 10% lanolin and 90% petrolatum, and mixed at 37° C. for 1 hour. Aliquants of the interferon antiviral preparation thus obtained were stored at 4° C. for 1 month, 6 months, 12 months, and 36 months.

Following each selected storage period, aliquants of interferon antiviral preparation were mixed with equal volumes of 5% fetal calf serum-containing tissue culture medium (Eagle's minimal essential medium) and incubated for 4 hours at 37° C., and the culture medium tested for eluted residual antiviral activity by the CPE inhibition assay. The results, expressed as % of initial antiviral activity, are shown in Table 4.

TABLE 4

Stability of interferon antiviral preparation (4° C.)

| Interferon | % Initial Activity storage time | | | |
|---|---|---|---|---|
| | 1 mo. | 6 mo. | 12 mo. | 36 mo. |
| Dodecyl amine-stabilized | 100 | 100 | 100 | 100 |
| Control | 70 | 10 | 0 | n.t.* |

*Signifies "not tested", because prior activity was already zero.

As shown, dodecyl amine treatment significantly stabilized the interferon antiviral preparation for periods of up to 36 months in samples stored at 4° C.

EXAMPLE 5

The interferon antiviral preparation in Example 4 was stored at room temperature (20°-24° C.). Results, expressed as % of initial antiviral activity, are shown in Table 5.

TABLE 5

Stability of interferon antiviral preparation (20-24° C.)

| Interferon | % Initial Activity storage time | | | |
|---|---|---|---|---|
| | 1 mo. | 6 mo. | 12 mo. | 36 mo. |
| Dodecyl amine-stabilized | 90 | 40 | 20 | 0 |
| Control | 0 | n.t.* | n.t. | n.t. |

*Signifies "not tested", because prior activity was already zero.

As shown, dodecyl amine treatment significantly stabilized the interferon antiviral preparation for periods of at least a year in samples stored at 20°-24° C.

EXAMPLE 6

TABLE 6

Stability of interferon antiviral preparation (37° C.)

| Interferon | % Initial Activity storage time | | | |
|---|---|---|---|---|
| | 1 mo. | 6 mo. | 12 mo. | 36 mo. |
| Dodecyl amine-stabilized | 50 | 20 | 0 | n.t.* |
| Control | 0 | n.t. | n.t. | n.t. |

*Signifies "not tested", because prior activity was already zero.

As shown, dodecyl amine-treatment significantly stabilized the interferon antiviral preparation for periods of up to six months in samples stored at 37° C.

EXAMPLE 7

The storage stability of interferon ointment was assessed. An interferon antiviral preparation was prepared as described in Example 4, with the exception that the pharmaceutical carrier contained 0.1% (weight %) dodecyl amine. Aliquants of the interferon ointments thus obtained were stored at 37° C., for 1 month, 6 months, 12 months, and 36 months. Aliquants were then mixed with equal volumes of 5% fetal calf serum-containing tissue culture medium (Eagle's minimal essential medium) and incubated for 4 hours at 37° C., and the culture medium tested for eluted residual antiviral activity by the CPE inhibition assay. The results are shown in Table 7.

TABLE 7

Stability of interferon ointment (4° C.)

| Interferon | % Initial Activity storage time | | | |
|---|---|---|---|---|
| | 1 mo. | 6 mo. | 12 mo. | 36 mo. |
| Dodecyl amine-ointment | 100 | 100 | 100 | 100 |
| Control | 70 | 10 | 0 | n.t.* |

*Signifies "not tested", because prior activity was already zero.

EXAMPLE 8

The interferon ointment as in Example 7 was stored at room temperature (20°-24° C.) for 1 month, 6 months, 12 months and 36 months. Results, expressed as % of initial antiviral activity, are shown in Table 8.

TABLE 8

Stability of interferon ointment (20-24° C.)

| Interferon | % Initial Activity storage time | | | |
|---|---|---|---|---|
| | 1 mo. | 6 mo. | 12 mo. | 36 mo. |
| Dodecyl amine-ointment | 100 | 100 | 100 | 100 |
| Control | 0 | n.t.* | n.t. | n.t. |

*Signifies "not tested", because prior activity was already zero.

EXAMPLE 9

Interferon ointments as in Example 7 were stored at 37° C. for 1 month, 6 months, 12 months and 36 months. Results, expressed as % of initial antiviral activity, are shown in Table 9.

TABLE 9

Stability of interferon ointment (37° C.)

| Interferon | % Initial Activity storage time | | | |
|---|---|---|---|---|
| | 1 mo. | 6 mo. | 12 mo. | 36 mo. |
| Dodecyl amine-ointment | 100 | 100 | 100 | 100 |
| Control | 0 | n.t.* | n.t. | n.t. |

*Signifies "not tested", because prior activity was already zero.

EXAMPLE 10

Leukocyte interferon extracted as in Example 1 was subjected to non-reducing SDS-PAGE and the alpha interferon and omega interferon fractions eluted into serum-containing medium (Eagle's minimal essential medium containing 5% fetal calf serum). Stabilized interferon compositions (1.0% by weight dodecylamine) as in Example 2 were prepared for alpha-isolate interferon and for omega-isolate interferon. Control interferon (containing both alpha and omega interferon) was prepared in saline. The stabilized interferon compositions were stored for up to one month at room temperature (20°-24° C.). Results are expressed as % of initial antiviral activity.

TABLE 10

Stabilization of stabilized interferon compositions: Alpha and omega interferon isolates (20°-24° C.)

| Interferon | % Initial Activity storage time | | |
|---|---|---|---|
| | 1 hr | 24 hrs | 1 month |
| Alpha-isolates | 100 | 100 | 100 |
| Omega-isolates | 100 | 100 | 100 |
| Control | 100 | 30 | 0 |

EXAMPLE 11

Stabilized interferon compositions comprising alpha isolate or omega isolate, as in Example 10, were stored for up to one month at 37° C. Results are expressed as % of initial antiviral activity.

TABLE 11

Stabilization of stabilized interferon compositions: Alpha and omega isolates (37° C.)

| Interferon | % Initial Activity storage time | | |
|---|---|---|---|
| | 1 hr | 24 hrs | 1 month |
| Alpha-isolates | 100 | 100 | 100 |
| Omega-isolates | 100 | 100 | 100 |
| Control | 100 | 30 | 0 |

EXAMPLE 12

Interferon ointments prepared as in Example 7 comprising alpha isolate or omega isolate (isolates prepared as in Example 10) were stored for up to 6 months at room temperature (20°-24° C.). Results are expressed as % of initial antiviral activity.

TABLE 12

Stability of interferon ointment: Alpha and omega isolates (20°-24° C.)

| Interferon | % Initial Activity storage time | |
|---|---|---|
| | 1 month | 6 months |
| Alpha-isolates | 100 | 100 |
| Omega-isolates | 100 | 100 |
| Control | 0 | n.t.* |

*Signifies "not tested", because prior activity was already zero.

EXAMPLE 13

Interferon ointments prepared as in Example 7 comprising alpha isolate or omega isolate (isolates prepared as in Example 10) were stored for up to 6 months at 37° C. Results are expressed as % of initial antiviral

TABLE 13

Stability of interferon ointment: Alpha and omega isolates (37° C.)

| Interferon | % Initial Activity storage time | |
|---|---|---|
| | 1 month | 6 months |
| Alpha-isolates | 100 | 100 |
| Omega-isolates | 100 | 100 |
| Control | 0 | n.t.* |

*Signifies "not tested", because prior activity was already zero.

Many other variations and modifications may be made in the invention hereinbefore described, by those having experience in this technology, without departing from the concept of the present invention. Accordingly, it should be clearly understood that the methods and compositions described in the foregoing description are illustrative only and not intended as a limitation on the scope of the invention.

What is claimed is:

1. A composition consisting essentially of a therapeutically effective amount of an interferon, which is an alpha interferon, an omega interferon, or a recombinantly produced interferon, and a stabilizing agent which is a primary alkyl amine, wherein the composition is free of agents for disrupting non-covalent bonds and agents for reducing disulfide bonds.

2. The composition of claim 1 which is a powder.

3. The composition of claim 2 wherein the powder is mixed with a pharmaceutically acceptable carrier.

4. The composition of claim 3 wherein the pharmaceutically acceptable carrier is petrolantum or lanolin.

5. The composition of claim 1 with an interferon activity of between about $10^4$ to about $10^6$ international units per milliliter.

6. The composition of claim 1 wherein the stabilizing agent comprises between about 0.1% to about 10% by weight of the composition.

7. The composition of claim 1 wherein the weight ratio of the stabilizing agent to the interferon is between about 1.00 to about 1.44.

8. The composition of claim 1 wherein the primary alkyl amine is an octyl amine, a decyl amine, a dodecyl amine, or a tetradecyl amine.

9. A composition consisting essentially of a therapeutically effective amount of an interferon, which is an alpha interferon, an omega interferon, or a recombinantly produced interferon, and a stabilizing agent which has the formula $Li_nRX$, wherein Li is lithium, R is an aliphatic, X is an anion, and n is a number chosen to electrochemically balance lithium with the anion, wherein the composition is free of agents for disrupting non-covalent bonds and agents for reducing disulfide bonds.

10. The composition of claim 9 which is a powder.

11. The composition of claim 10 wherein the powder is mixed with a pharmaceutically acceptable carrier.

12. The composition of claim 11 wherein the pharmaceutically acceptable carrier is petrolatum or lanolin.

13. The composition of claim 9 with an interferon activity of between about $10^4$ to about $10^6$ international units per milliliter.

14. The composition of claim 9 wherein the stabilizing agent comprises between about 0.1% to about 10% by weight of the composition.

15. The composition of claim 9 wherein the weight ratio of the stabilizing agent to the interferon is between about 1.00 to about 1.44.

16. The composition of claim 9 wherein the stabilizing agent is a lithium octyl sulfate, a lithium decyl sulfate, a lithium dodecyl sulfate, or a lithium tetradecyl sulfate.

17. A method for making a composition wherein the composition is free of agents for disrupting non-covalent bonds and agents for reducing disulfide bonds comprising the steps of:
   a. providing an amount of interferon which is an alpha interferon, an omega interferon, or a recombinantly produced interferon,
   b. mixing the provided interferon with an effective amount of a stabilizing agent which is a primary alkyl amine to form the composition; and
   c. dialyzing the composition.

18. The method of claim 17 further comprising the step of lyophilizing the dialyzed composition to a powder.

19. The method of claim 18 wherein the powder is mixed with a pharmaceutically acceptable carrier.

20. The method of claim 19 wherein the pharmaceutically acceptable carrier is petrolatum or lanolin.

21. The method of claim 17 wherein the composition has an interferon activity of between about $10^4$ to about $10^6$ international units per milliliter.

22. The method of claim 17 wherein the stabilizing agent comprises between about 0.1% to about 10% by weight of the composition.

23. The method of claim 17 wherein the weight ratio of the stabilizing agent to the interferon is between about 1.00 to about 1.44.

24. The method of claim 17 wherein the primary alkyl amine is an octyl amine, a decyl amine, a dodecyl amine, or a tetradecyl amine.

25. A composition made by the method of claim 17.

26. A method for making a composition wherein the composition is free of agents for disrupting non-covalent bonds and agents for reducing disulfide bonds comprising the steps of:
   a. providing an amount of interferon which is an alpha interferon, an omega interferon, or a recombinantly produced interferon,
   b. mixing the provided interferon with an effective amount of a stabilizing agent which has the formula $Li_nRX$, wherein Li is lithium, R is an aliphatic, X is an anion, and n is a number chosen to electrochemically balance lithium with the anion to form the composition; and
   c. dialyzing the composition.

27. The method of claim 26 further comprising the step of lyophilizing the dialyzed composition to a powder.

28. The method of claim 27 wherein the powder is mixed with a pharmaceutically acceptable carrier.

29. The method of claim 28 wherein the pharmaceutically acceptable carrier is petrolatum or lanolin.

30. The method of claim 26 wherein the composition has an interferon activity of between about $10^4$ to about $10^6$ international units per milliliter.

31. The method of claim 26 wherein the stabilizing agent comprises between about 0.1% to about 10% by weight of the composition.

32. The method of claim 26 wherein the weight ratio of the stabilizing agent to the interferon is between about 1.00 to about 1.44.

33. The method of claim 26 wherein the stabilizing agent is a lithium octyl sulfate, a lithium decyl sulfate, a lithium dodecyl sulfate, or a lithium tetradecyl sulfate.

34. A method made by the method of claim 26.

* * * * *

UNITED STATES PATENT AND TRADEMARK OFFICE
CERTIFICATE OF CORRECTION

PATENT NO. : 5,236,707
DATED : August 17, 1993
INVENTOR(S) : William E. Stewart, II It is certified that error appears in the above-identified patent and that said Letters Patent is hereby corrected as shown below:

Column 12, line 37, change "consisting essentially of" to -- comprising --;

Column 12, line 61, change "consisting essentially of" to -- comprising --.

Column 14, line 44, change "A method made" to -- A composition made --.

Signed and Sealed this

Twenty-eighth Day of June, 1994

*Attest:*

BRUCE LEHMAN

*Attesting Officer*          Commissioner of Patents and Trademarks